(12) United States Patent
Rajagopal

(10) Patent No.: US 11,731,819 B2
(45) Date of Patent: Aug. 22, 2023

(54) DEVICES, SYSTEMS, AND METHODS FOR SENSING THE OPENING OF PHARMACEUTICAL BOTTLES

(71) Applicant: Deven Rajagopal, Atlanta, GA (US)

(72) Inventor: Deven Rajagopal, Atlanta, GA (US)

( * ) Notice: Subject to any disclaimer, the term of this patent is extended or adjusted under 35 U.S.C. 154(b) by 0 days.

(21) Appl. No.: 17/817,293

(22) Filed: Aug. 3, 2022

(65) Prior Publication Data

US 2022/0411148 A1 Dec. 29, 2022

Related U.S. Application Data

(60) Provisional application No. 63/260,011, filed on Aug. 6, 2021.

(51) Int. Cl.
| | | |
|---|---|---|
| *G08B 1/08* | (2006.01) | |
| *B65D 55/02* | (2006.01) | |
| *B65D 55/14* | (2006.01) | |
| *A61J 1/03* | (2023.01) | |
| *B65D 51/24* | (2006.01) | |

(52) U.S. Cl.
CPC .............. *B65D 55/026* (2013.01); *A61J 1/03* (2013.01); *B65D 51/245* (2013.01); *B65D 55/028* (2013.01); *B65D 55/145* (2013.01); *B65D 2555/02* (2013.01); *B65D 2585/56* (2013.01)

(58) Field of Classification Search
CPC .. B65D 55/026; B65D 51/245; B65D 55/028; B65D 55/145; B65D 2555/02; B65D 2585/56; A61J 1/03; A61J 2200/70; A61J 2205/20; A61J 2205/60; A61J 2205/70; G16H 20/13; G16H 40/63

USPC ........................................................ 340/539.1
See application file for complete search history.

(56) References Cited

U.S. PATENT DOCUMENTS

| | | | |
|---|---|---|---|
| 7,554,434 | B1 | 6/2009 | Gifford |
| 7,907,477 | B2 * | 3/2011 | Puzia ................... G04G 13/026 |
| | | | 215/230 |
| 10,874,590 | B1 * | 12/2020 | Butaud ................. A61J 7/0046 |
| 2006/0124655 | A1 | 6/2006 | Ratnakar |
| 2010/0006585 | A1 * | 1/2010 | Flowers ................ A61J 7/0409 |
| | | | 221/7 |
| 2014/0262918 | A1 | 9/2014 | Chu |
| 2014/0266760 | A1 | 9/2014 | Burke, Jr. |
| 2016/0120758 | A1 | 5/2016 | Pi |
| 2017/0281467 | A1 * | 10/2017 | Solotoff ................ A61J 1/1437 |

OTHER PUBLICATIONS

International Search Report and Written Opinion for PCT/US2022/074486, 6 pages (dated Oct. 28, 2022).

\* cited by examiner

*Primary Examiner* — Tai T Nguyen
(74) *Attorney, Agent, or Firm* — FisherBroyles LLP; Anthony J DoVale

(57) ABSTRACT

A system for sensing use of a pharmaceutical bottle may include a housing, a sensing plate mechanically coupled to the housing by a flexible expansion member, an activation plate mechanically coupled to the sensing plate, an electronic contact on the housing, an electrical circuit formed by the contact on the housing and the activation plate, an indicator configured to indicate use of the pharmaceutical bottle, a user interface configured to receive user input to control the indicator, and a processor and memory with instruction that when execute by the processor cause the system to determine that the pharmaceutical bottle has been used based on a change in the electrical circuit.

17 Claims, 13 Drawing Sheets

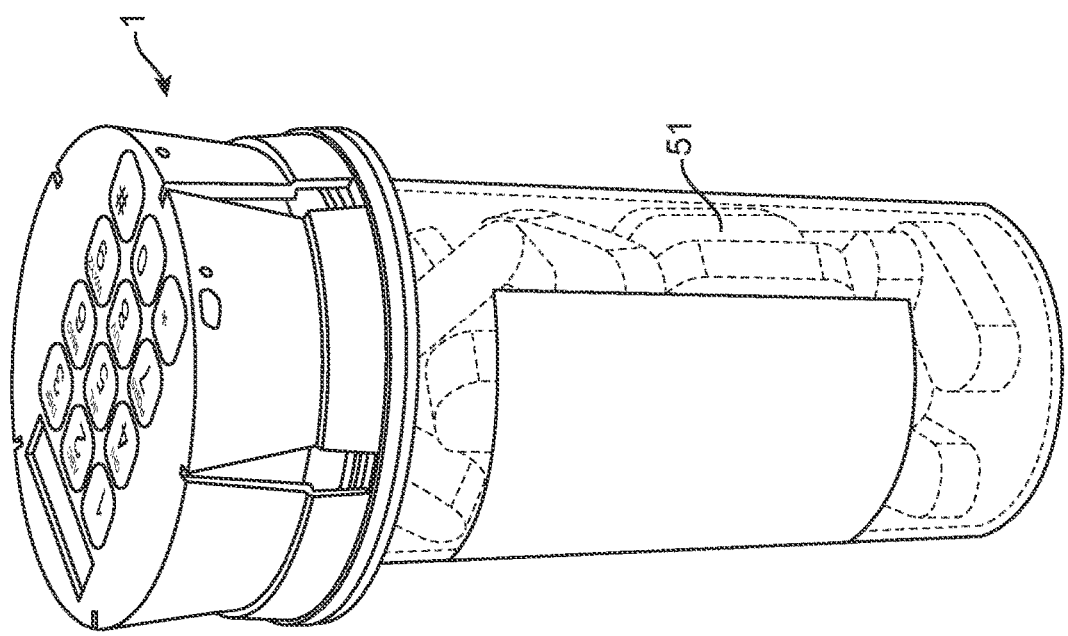
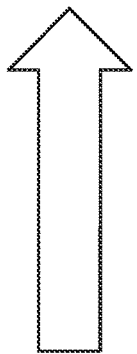
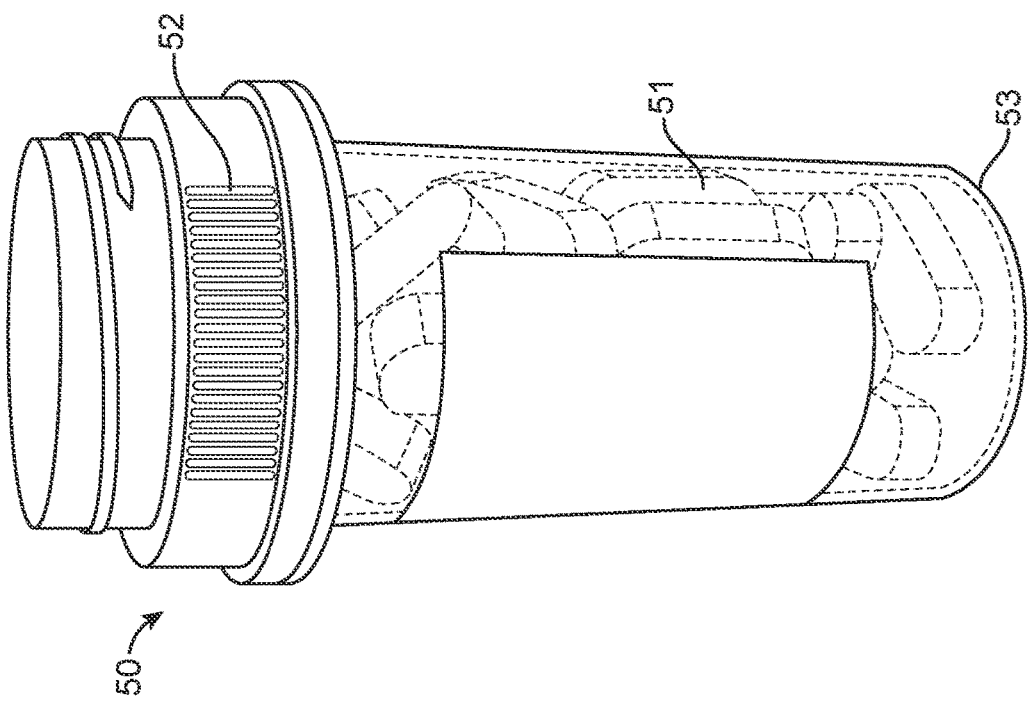

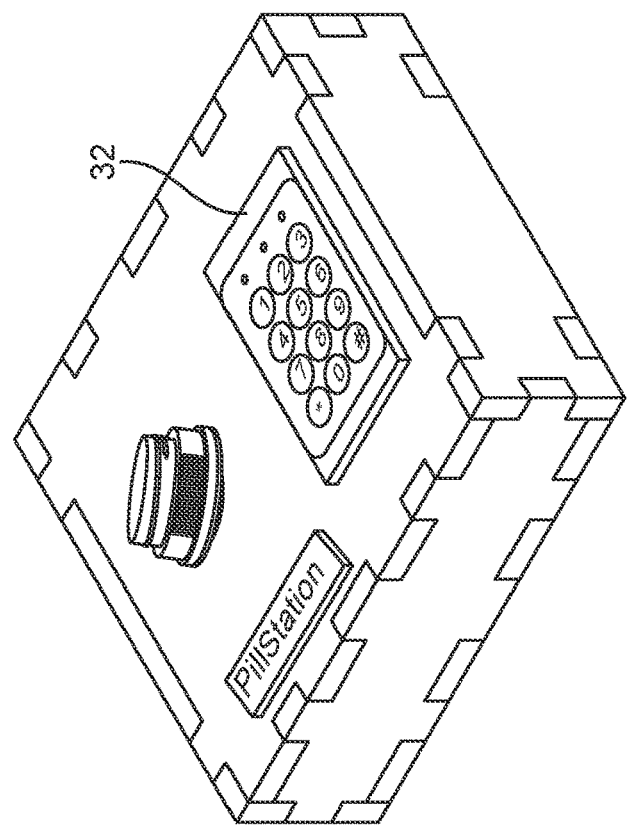
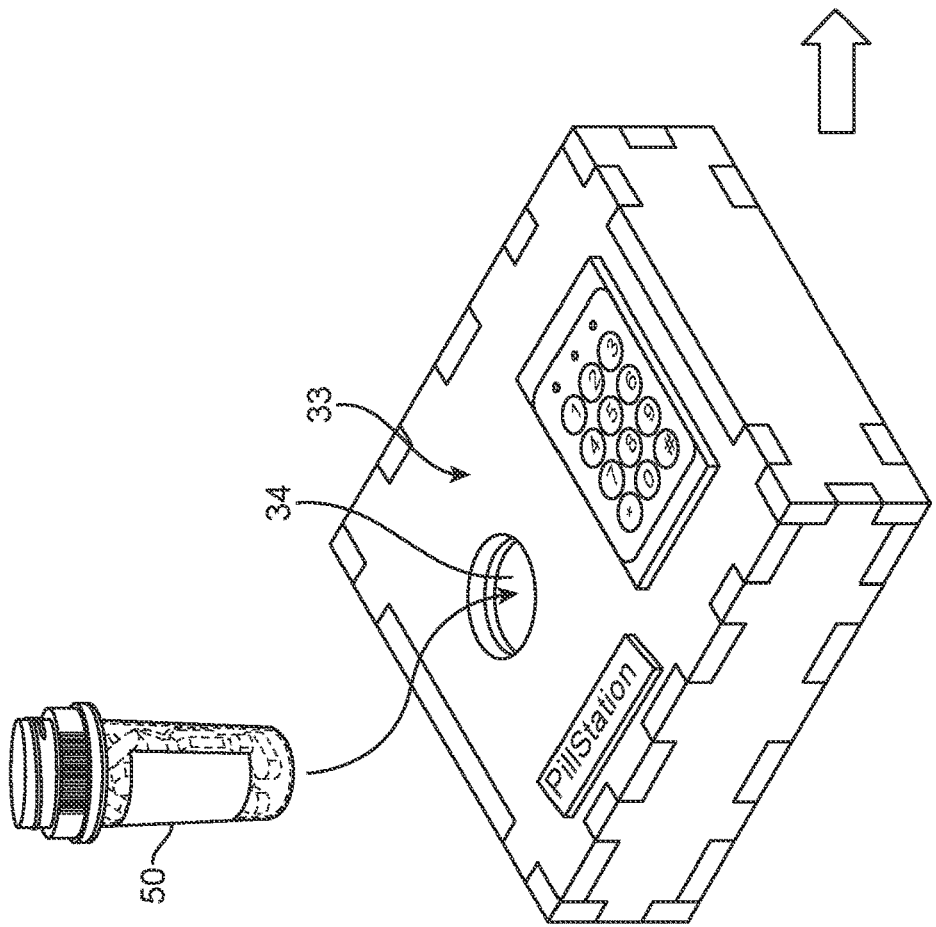
FIG. 10B
FIG. 10A

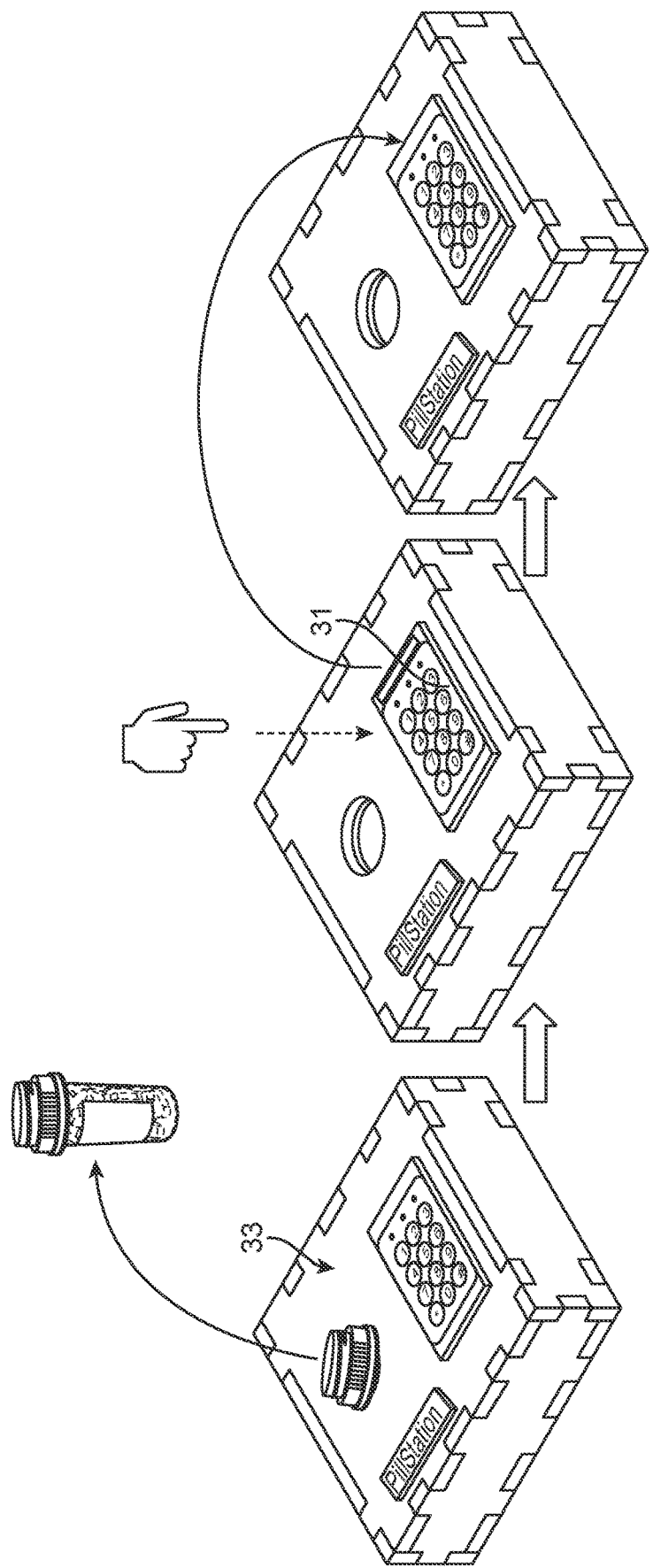

DEVICES, SYSTEMS, AND METHODS FOR SENSING THE OPENING OF PHARMACEUTICAL BOTTLES

RELATED APPLICATIONS

This application claims the benefit under 35 U.S.C. § 119(e) of U.S. Provisional Patent Application No. 63/260,011, filed Aug. 6, 2021, which is incorporated, in its entirety, by this reference.

FIELD OF INVENTION

The present invention relates generally to devices, systems, and methods for sensing when a pharmaceutical bottle is opened. More specifically, when the devices, systems, and methods sense that a pharmaceutical bottle is opened, they may provide a visual and/or auditory signal based on the opening and may communicate this signal to a user's smart phone. Turning the signal off may require entry of a digital or biometric code and/or signature directly on the device or system or via entry on the smart phone. The visual and/or auditory signal may also be turned off or prevented from being turned on by a "digital handshake" between the device and the smart phone when the pharmaceutical bottle is being opened.

BACKGROUND OF THE INVENTION

Although abuse of illicit drugs has long been a public health crisis and garnered much attention, abuse of prescription medications, such as opioids and amphetamine analogues, has also created a crisis of similar magnitude. This crisis has grown as amphetamine-like drugs have been increasingly prescribed for attention-deficit disorder (ADD) or attention-deficit hyperactivity disorder (ADHD), and as opioids have been increasingly prescribed for chronic pain disorders.

Although opioids can be essential to treat chronic pain, over the last several decades the widespread distribution and use of opioids, for both medical and nonmedical reasons, has resulted in an opioid epidemic. According to the National Institute on Drug Abuse, more than 1.7 million Americans suffered from opioid abuse in 2017, including 652,000 with heroin use disorder, and more than 47,000 Americans dying each year as a result of an opioid overdose. Unfortunately, the recent COVID-19 pandemic has exacerbated the opioid crisis. Because of increased economic distress, social isolation, and mental health disorders, the COVID-19 pandemic has led to increasing abuse of prescription opioids, heroin, and synthetic opioids. In fact, the American Medical Association has warned that at least 30 states have reported an increase in opioid-related deaths since the start of the pandemic.

At particular risk for this "epidemic within a pandemic" are US adolescents, who have suffered high levels of loneliness, social isolation, anxiety, and depression, and are prone to opioid use and abuse. For example, from 1976 to 2015, up to one fourth of high school seniors reported medical or nonmedical use of prescription opioids (McCabe S E et. al. Pediatrics. 2017 April; 139(4): e20162387. doi: 10.1542/peds.2016-2387. Epub 2017 Mar. 20.) This trend is likely to continue or worsen because of the COVID-19 pandemic.

It is not uncommon for adolescents' first exposure to opioids to occur when they obtain opioids from a prescription pill bottle belonging to a family or friend, who are often not aware of the abuse. Similarly, adolescents might experiment with prescription stimulants by obtaining these medications from prescription pill bottles of family members. In fact, because these medications are not widely seen as addictive like opioids, it is more likely that such experimentation will not be detected.

Several approaches to reduce nonmedical use and experimentation have been developed, but each approach has limitations that might reduce uptake of these technologies. The most stringent approach is locking the prescription bottle with either a locking cap or locking container. For example, the SaferLock™ cap (Safer Lock, Sacramento, Calif.) is a pill bottle cap with a combination lock that cannot be opened unless a four-digit code is entered. This approach is less than ideal for many reasons. For example, many chronic opioid users, who are often older with multiple comorbidities, including memory issues, might be hesitant to use a locking container for fear of forgetting the code, thereby creating a medication crisis when they most need the pain medicine. Even though the cap has a reset pin, many users will be scared of losing the pin, thereby preventing themselves from resetting the code if they forget it. Similarly, locking containers such as the Safer Lock Box (Safer Lock, Sacramento, Calif.), SafeRX locking pill bottle (Safe Rx, Greenwood Village, Colo.), the Vaultz (Vaultz, Cleveland, Ohio), Pill Pod (Novato, Calif.), or LockMed (Pittsburgh, Pa.) all suffer similar limitations.

SUMMARY

Presented herein are devices, systems, and methods that can be used to sense when a pharmaceutical bottle is moved or opened. The system may include a sensing mechanism that detects when a bottle is moved or opened, a visual and/or auditory indicator that activates with bottle opening, and an interface that accepts analog or digital data to turn the indicator off. The disclosed devises, systems, and methods may also include wireless communication between containers and with smartphones.

In one aspect disclosed herein, the sensing mechanism may be integrated into a cap of a bottle, into a container that can receive a bottle, or into a pill bottle station that can accept the bottle therein. In another aspect, the sensing mechanism may include one or more mechanical switches with or without connection to an electrical circuit, such as an electro-mechanical switch, or a pressure-sensing system connected to an electrical circuit. A switch may toggle from one state to another state when a cap is screwed or unscrewed from the bottle or when the bottle is placed into or removed from a container. A mechanical switch may transmit a signal directly to the indicator system or via intervening elements such as springs, levers, bars, hinges, doors, rachets or the like, to another mechanical component, such as a spring, lever, bars, hinges, doors, rachets or the like and then to the indicator system. Alternatively, the switch may transmit a signal directly, or via intervening elements as above, to an electrical circuit, which connects directly or indirectly to the indicator system.

Alternatively, the sensing system may be a pressure-sensing system that detects pressure differences and may transmit a signal to the indicator system via an electrical circuit. In some embodiments, a pressure-sensing system may include any known type of pressure sensor, micro-switch, magnetic detection switch, or piezoelectric crystal.

In some embodiments, such as, for example, when the sensing mechanism is integrated into a bottle cap, the "off" state of the sensing system, resulting signal, and/or indicator may be when the cap is screwed onto the bottle, and the "on"

state may be when the cap is unscrewed. The indicator may be activated in the "on" state. If the sensing mechanism is integrated into the bottle container, the "off" state is when the bottle is resting in the container, and the "on" states is when the bottle is removed from the container. The indicator may be activated in the "on" state.

In another aspect, the visual indicator can be a morphological or color change to the bottle cap or container, or a visual display on the bottle cap or container. The morphological change may be one or more members, that may take the shape of any polyhedron, that may expand outwards from a surface of the cap or container or may collapse inwards from the surface of either a bottle cap or container. With respect to color change, any part of the bottle or container may change from one or more colors to one or more different colors when the sensing mechanism is activated, such as the cap, the bottle body, or other part of the bottle, such as a bottom surface of the bottle.

With respect to a visual display, the indicator can be one or more lights, such as, for example, light-emitting diodes (LED), OLED, or phosphorescent LED, TOLEDS, AMOLEDS, PMOLEDS, or QLEDS. The one or more lights can be placed anywhere on the cap of the bottle or on the body of the bottle container. In some embodiments, the visual indicator may be a liquid crystal display (LCD) that may display any shape or text when the sensing mechanism is activated. Other types of indicators include electronic ink displays, haptic feedback devices, or other visual, auditory, or other sensory indicators.

In another aspect, once the visual or other indicator is activated, data may be inputted into a user interface to disable or reset the indicator. The interface may be either integrated into the container, such as a bottle or bottle cap, or integrated into a bottle container, such as the body of the bottle, including the sidewalls, rim opening, and bottom of the bottle. The data may be checked to see if it matches data for turning off, resetting, or disabling the indicator. The data for resetting or disabling the indicator may be data initially provided by the user via the user interface, such as when the device was first activated.

Alternatively, or in addition, the user interface may receive analog data such as through buttons that are pressed or dials that are turned. These analogue interfaces may activate physical mechanisms to toggle the visual indicator back to the "off" state. Alternatively, the user interface could accept digital data; such as an alphanumeric code or biometric data such as fingerprints converted into computer data. An algorithm may analyze the received data to determine if it matches the initial data inputted into the system. If they match, the algorithm may turn the visual indicator off.

In practice, a user may initialize the system or device, such as a bottle cap or bottle container with user-specific data, for example a password or passcode, before or after either the bottle cap is placed onto the pharmaceutical bottle or the bottle is placed in the bottle container. Then, when either the cap is unscrewed, or the bottle is removed from the container, the visual indicator may activate to indicate the opening or removal of the bottle. Then, before or after the cap is screwed back on or the bottle is placed back into the container, the user would input data to turn off the visual indicator. Therefore, anyone other than the user, including someone who does not know the password, will not be able to turn off the visual indicator, which would indicate that the bottle had been opened or moved by someone without permission to access the pharmaceutical bottle.

In another aspect, communication between the bottle cap, bottle container, or pill bottle station and a smartphone can occur when the bottle is being opened. Specifically, when the bottle is being opened, the system can emit a wireless signal, for example, a signal to an authorized user's smartphone. If the authorized user's smartphone is in a certain vicinity of the system the smartphone and receives the signal from the bottle cap, bottle container, or bill pottle station, then the smartphone may send a signal back to the system indicating that the authorized user is close to the system. In such embodiments, the system may not activate the visual indicator. If the smartphone is not in a certain vicinity of the system or otherwise does not respond to the signal, then the smartphone may not give an "all clear" signal, and the system may activate its visual indicator to indicate that an unauthorized user has opened the bottle. The system may also send a message to the authorized user's smartphone indicating that the bottle has been opened without permission.

In another aspect, the user may use a smartphone app to set the operational mode for the system. For example, the user may send a signal via the app to turn off the alert and indication system or modify the conditions for when a warning signal should be sent. For example, the smartphone application may alert a user if bottle is opened outside certain time periods or if bottle is opened more than a certain number of times. The user may also use the smartphone app to put the system in a "lockdown" mode. In lockdown mode, when the bottle is being opened, the system may send a signal looking for the authorized user's smartphone. If the smartphone receives signal, it may send a signal, such as an "all clear" signal, back to the system, and the bottle may be opened. If the smartphone, because of being outside the predefined vicinity of the system, does not send a signal, such as an "all clear" signal, back to the system, the system may prevent the bottle from being opened.

In another aspect, the bottle cap, bottle container, or pill bottle station communicates with either a passive or active radio frequency identification (RFID) tag worn by the user. If a passive RFID tag is used, then the bottle cap, bottle container, or pill bottle station transmits energy to the tag, which will read the signal and transmit information back, sending an "all clear" signal, either to turn off any alert or to allow the bottle to be opened. Alternatively, the RFID tag may be active, like a beacon, which transmits regular signals that can be picked up by the reader embedded in the pill bottle system when the system is in close proximity to the tag.

DESCRIPTION OF THE FIGURES

FIG. 3 depicts a perspective view of a prescription pill bottle, according to one or more embodiments herein;

FIG. 4 depicts a perspective view of a prescription pill bottle with its standard cap replaced by a pill bottle cap, according to one or more embodiments herein;

FIG. 10A depicts a perspective view of a prescription bottle being placed into a pill bottle station, according to one or more embodiments herein;

FIG. 10B depicts a perspective view of a prescription bottle placed onto the docking port of the pill bottle station, according to one or more embodiments herein;

FIG. 11A depicts a perspective view of a pill bottle station illustrating removal of a pill bottle therefrom, according to one or more embodiments herein;

FIG. 11B depicts a perspective view of the pill bottle station indicator light activated and illustrating a security code being entered, according to one or more embodiments herein;

FIG. 11C depicts a perspective view of the pill bottle station after the security code has been entered with the indicator light turned off, according to one or more embodiments herein;

DESCRIPTION OF THE INVENTION

Figure 2:
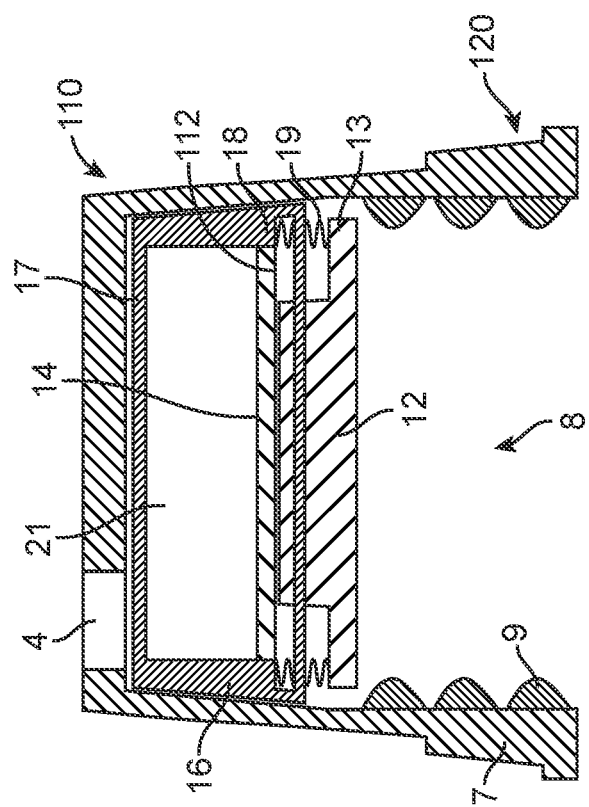
FIG. 2 depicts a cross-sectional side elevational view of the pill bottle cap, according to one or more embodiments herein.

The present disclosure can be understood more readily by reference to the following detailed description, examples, and claims, and their previous and following description. Before the present system, devices, and/or methods are disclosed and described, it is to be understood that this disclosure is not limited to the specific systems, devices, and/or methods disclosed unless otherwise specified, as such can, of course, vary. It is also to be understood that the terminology used herein is for the purpose of describing particular aspects only and is not intended to be limiting.

The following description of the disclosure is provided as an enabling teaching in its best, currently known aspect. Those skilled in the relevant art will recognize that many changes can be made to the aspects described, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

As used herein, the singular forms "a," "an" and "the" include plural referents unless the context clearly dictates otherwise. Thus, for example, reference to a "tether" includes aspects having two or more tethers unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The application relates to devices and systems used to sense the opening of pharmaceutical bottles 50. More specifically, the application relates to pill bottle caps 1 (see, e.g. FIGS. 1-8), pill bottle stations 30 (see, e.g. FIGS. 9-11), and pill bottle containers 70 (see, e.g., FIGS. 12-18), and related methods (see FIGS. 19 and 20). The pill bottle cap 1 has a sensing plate 12, indicator panel 4, and a passcode pad 3. The pill bottle station 30 has a sensing plate 34, indicator panel 32, and passcode pad 31. The pill bottle container 70 has a sensing plate 82, indicator panel 74, and passcode pad 73.

The Pill Bottle Cap

Figure 1:
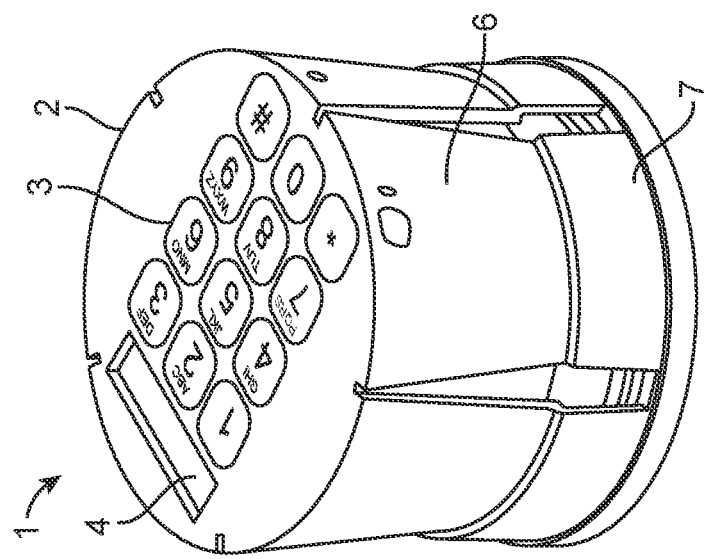
FIG. 1 depicts a perspective view of the pill bottle cap, according to one or more embodiments herein.
Figure 6:
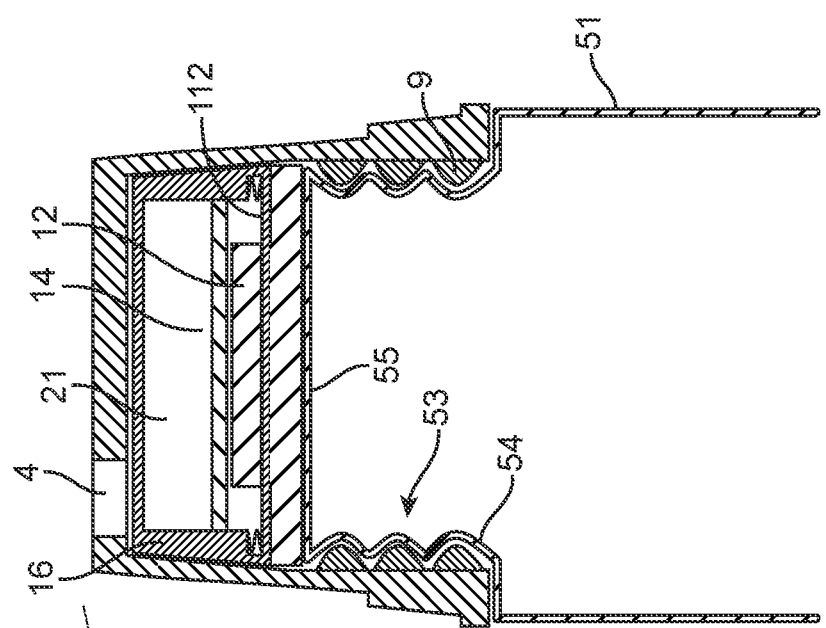
FIG. 6 depicts a cross-sectional side elevational view of the prescription bill bottle connected to the pill bottle cap of FIG. 5, according to one or more embodiments herein.
Figure 5:
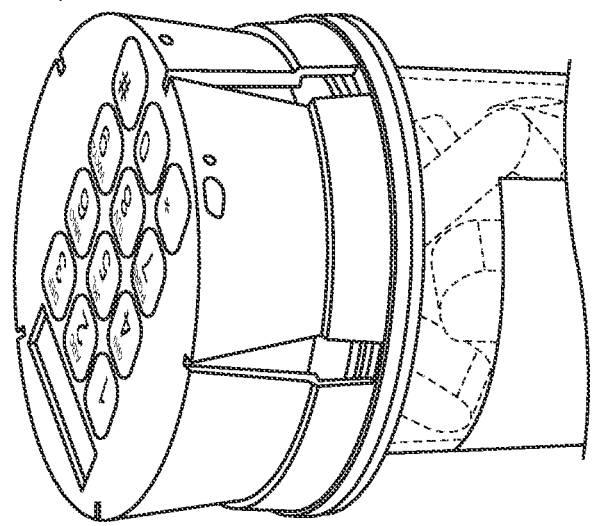
FIG. 5 depicts a perspective view of upper part of a prescription pill bottle connected to a pill bottle cap, according to one or more embodiments herein.

Now referring to FIGS. 1-2, the pill bottle cap 1 includes a top 2 housing, and indicator 4, and a user input interfaces, such as a passcode pad 3. Top 2 may be circular, elliptical, or comprise any polygonal shape, and be composed of any metal, plastic polymer, or combination thereof. The top 2 may have a diameter suitable for manipulation by a user and the diameter may be the same or different than the body 6 of the pill bottle cap 1. Similarly, indicator 4 may take any shape. The indicator 4 may be recessed into or protruding above top 2. The indicator 4 may be a visual indicator, such as a light and display and may house LED, LCD, magnetic, mechanical, nonelectric, electro-mechanical or other visual elements, as described herein. Passcode pad 3 may contain one or more alphanumeric elements for receiving user input, such as a touch pad, push buttons, or rotary dials. For purposes of illustration, an alphanumeric passcode pad is shown. In some embodiments, the user input interface may be a fingerprint reader or other biometric input or scanning device and may receive or read biometric data.

The body may extend from the top 2 to the bottom 7. In some embodiments, the top 2 connects via the body 6 to the bottom 7. The body 6 and bottom 7 may have a diameter, thickness, or shape suitable for manipulation by a user. The body may be composed of any of any metal, plastic polymer, or combination thereof. The body 6 may form a cavity 8 having an opening towards the bottom 7 of the body 6. The cavity may be defined by the inside of the wall 120 that extends from the bottom 7 towards to the top 2. Threads 9 may be formed, or extend, from an inner facing surface of the walls 120.

A sensor or sensor system 110 may be located within the body 6 and/or within the cavity 8. The sensor system 110 may include a sensing plate 12 mechanically coupled to a circuit housing 16 via flexible expansion elements 19, which may be springs or coils. The expansion elements may be non-conductive or may be insulated from the circuit housing 16. The expansion elements push against the perimeter or corners 18 of the circuit housing 16 and/or extension or compression tabs 13 that extend outward from the sensing plate 12. The expansion elements push the activating plate into contact and electrical continuity with the circuit 21 contacts 112. When the cap 1 is free of a bottle, the activation plate 14 touches or is in electrical continuity with the contacts 112 of the circuit 21. When the cap 1 is coupled to a bottle, the sensing plate 12 pushes the activation plate 14 away from the contacts, opening the circuit 21 within circuit housing 16. The sensor system 110 may also include an RFID system therein, such as a processor, power source, antenna, transmitter, reader and non-transitory memory including instruction for authenticating an RFID tag.

Now referring to FIGS. 3-4, which depict a process for replacing a standard cap 52 with a smart cap, such as the cap 1 that is shown and described with reference to FIGS. 1 and 2. First, the standard cap 52 may be removed from the body 51 of a pharmaceutical bottle 50 by rotating the standard cap 52 off of the body 51 of a pharmaceutical bottle 50. A smart cap, such as the pill bottle cap 1, may then be screwed onto body 51 of the standard pharmaceutical bottle 50. As illustrated if FIGS. 5-6, the threads 9 of pill bottle cap 1 are complementary to the threads 54 of the pharmaceutical bottle 50, allowing cap 1 to be screwed onto body 51 of bottle 50. When screwed on, the upper lip 55 of body 51 pushes sensing plate 12, compressing the flexible expansion elements 19, and pushing the activation plate 14 upward into the circuit 21 within the circuit housing 16 into electrical contact and continuity with the contacts 112. When the cap 1 has been initially activated, this configuration is the inactive state of the circuit, and the indicator 4 is off. The display may prompt a user to input a code to activate the sensor. This code may be used later to deactivate the tamper indicator during normal use.

Figure 8:
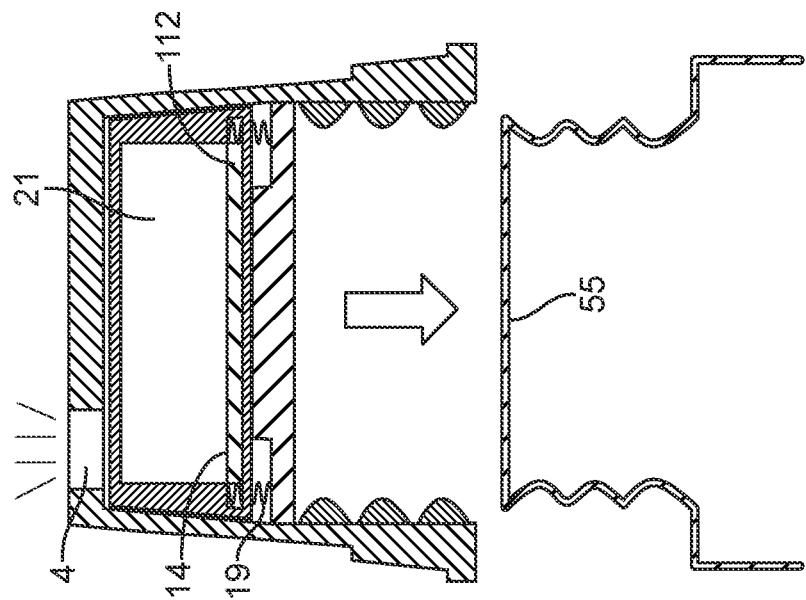
FIG. 8 depicts a cross-sectional side elevational view of pill bottle cap with pill bottle disengaged and indicator light on, according to one or more embodiments herein.
Figure 7:
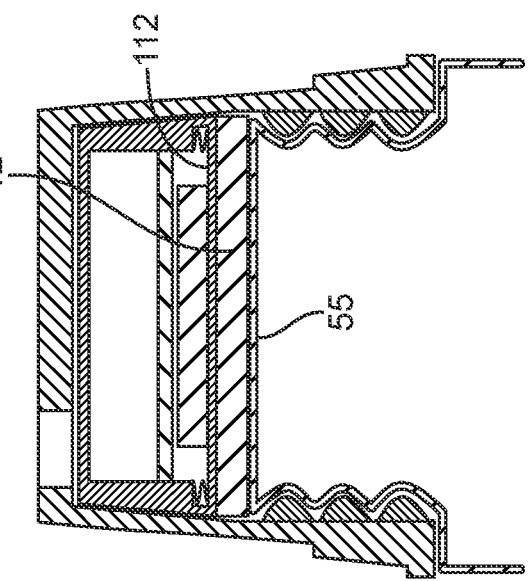
FIG. 7 depicts a cross-sectional side elevational view of FIG. 6, according to one or more embodiments herein.

Now referring to FIG. 7-8, when the body 51 of bottle 50 is unscrewed from cap 1, the rim 55 no longer pushes the sensing plate 12. In this state, the one or more flexible compression elements 19 expand, causing the sensing plate 12 and attached activation plate 14 to descend, thereby breaking continuity and activating the indicator 4, indicating that cap 1 has been removed from body 51 of bottle 50. In some embodiments, in order for circuit to be deactivated, cap 1 has to be screwed back onto body 51 of bottle 50 and the security code has to be entered into the passcode pad 3. If the code is not entered, then the visual indicator remains activated, indicating that the cap 1 has been removed and replaced by a non-intended user.

While the above has been described with respect to the sensing plate contacting contacts 112 with continuity between the sensing plate and contacts 112 occurring when the cap is installed and no continuity with the cap is removed, in some embodiments, the activation plate may be in electrical continuity with the cap is removed and not in electrical continuity when the cap is installed. In some embodiments, the system may determine cap installation and removal based on a combination of continuity and/or lack thereof between the sensing plate and the contacts 112 and between the activation plate and the contacts 112.

Figure 9:
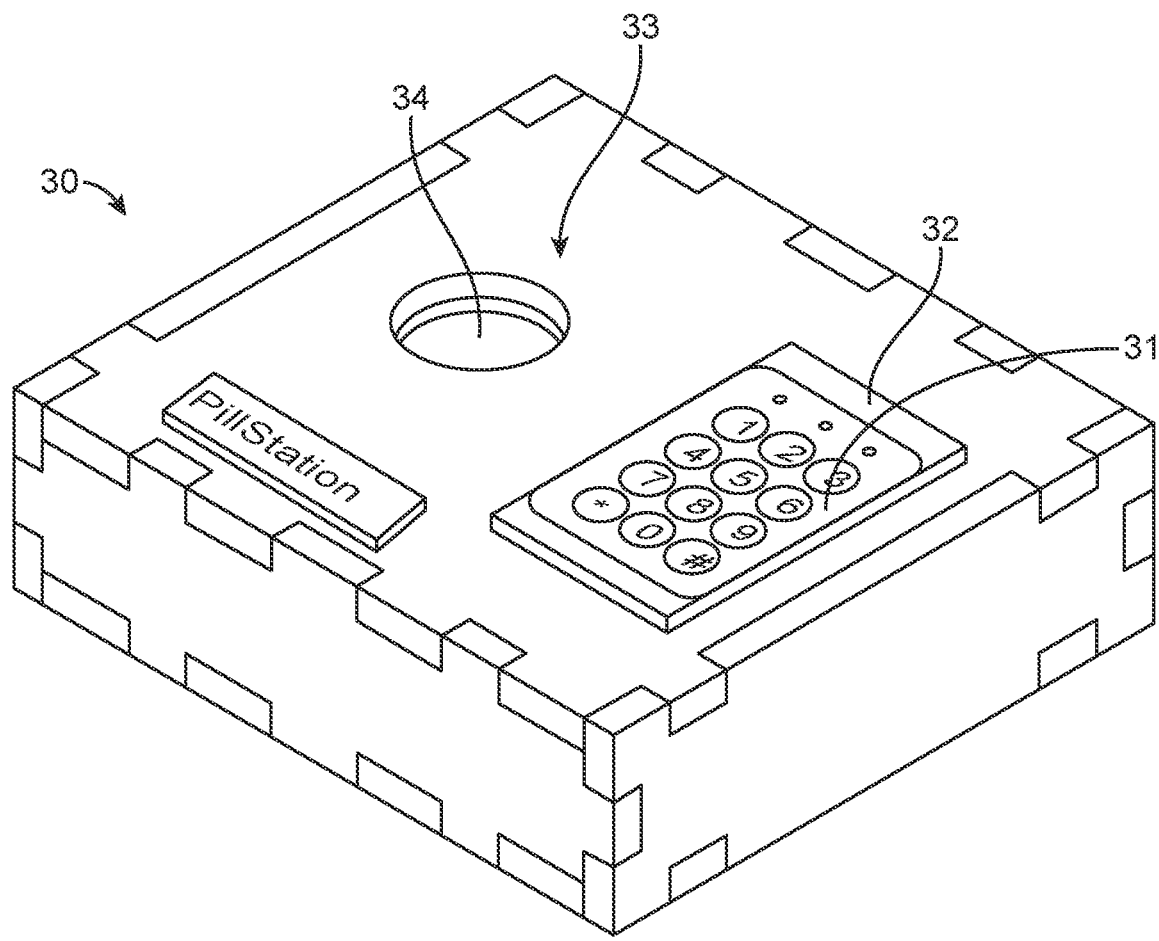
FIG. 9 depicts a perspective view of a pill bottle station, according to one or more embodiments herein.

The Pill Bottle Station (FIGS. 9-11)

Now referring to FIG. 9, the pill bottle station 30 may be of any dimension, shape, and thickness, and may be made from any of wood, plastic, or metallic components or combinations thereof. The pill bottle station 30 has one or more docking stations 33, which have a recess with a sensing plate 34. The pill bottle station also has an indicator 32 and user interface 31. Like the plate, indicator, and passcode pad of the pill bottle cap 1, these elements of the pill bottle station may be of any morphology or material composition, as described herein.

Now referring to FIG. 10A-B, upon initial use of the station, the pharmaceutical bottle 50 is placed onto the sensing plate 34 of the one or more docking stations 33. In this state, the visual indicator 32 is off. FIGS. 11A-11C illustrate activation of the visual indicator 32. To open the bottle 50, as user removes it from the docking station 33. The station may include a sensor system 110, such as described above. When the bottle 50 is removed from docking station 33, pressure is relieved from sensing plate 34, thereby activating a circuit, such as the circuit described above with respect to sensor system 110, which turns on visual indicator 32. To turn off visual indicator 32, a code may be entered via the passcode pad 31, returning the pill bottle station 30 to its baseline state. If the correct code is not entered via the passcode pad 31, the visual indicator 32 remains on even if the pharmaceutical bottle 50 is placed back into the docking station, indicating unauthorized use.

As with the sensor system 110, while the above has been described with respect to the sensing plate, activating and sending a signal when pressure is relieved from the sensing plate 34, in some embodiments, the sensing plate may be in electrical continuity with the bottle is on the sensing plate and not activated when the bottle is removed.

The station may include a sensor system, such as sensor system 110, which may incorporate the sensing plate 34, which may be similar to sensing plate 12. The sensor system 110 within the station may include an RFID system, such as a processor, power source, antenna, transmitter, reader and non-transitory memory including instruction for authenticating an RFID tag.

The Pill Bottle Container (FIGS. 12-18)

Figure 12:
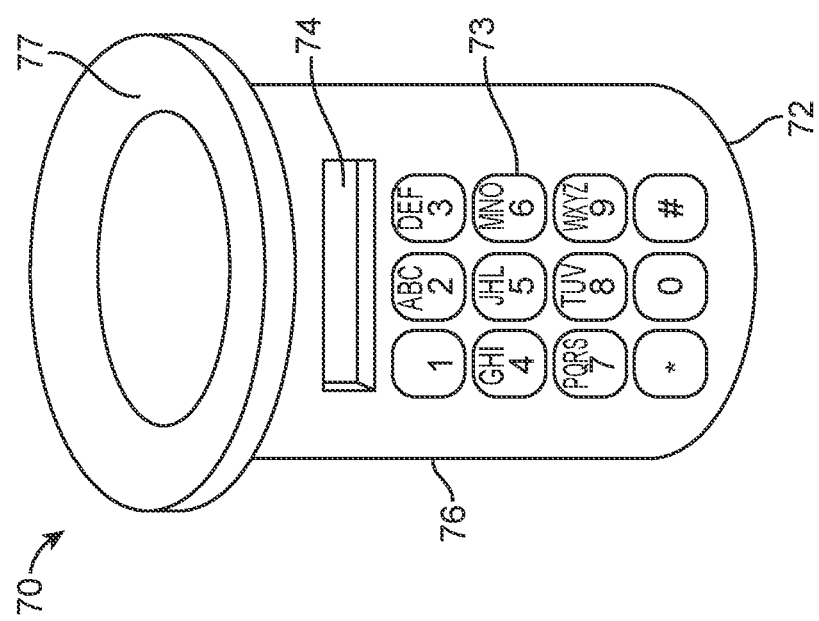
FIG. 12 depicts a perspective view of a pill bottle container, according to one or more embodiments herein.

Referring to FIG. 12, a pill bottle container 70 comprises a top 77, indicator 74, body 76, passcode pad 73, and bottom 72. Top 77 preferentially has a large diameter than body 76, but like the analogous elements of the pill bottle cap or the pill bottle station, the top 77, indicator 74, body 76, passcode pad 73, and bottom 72 can be of any morphology, size, or thickness, and contain plastic and/or metallic elements. The indicator 74 and passcode pad 73 can be located anywhere on the surface of body 76.

Figure 13:
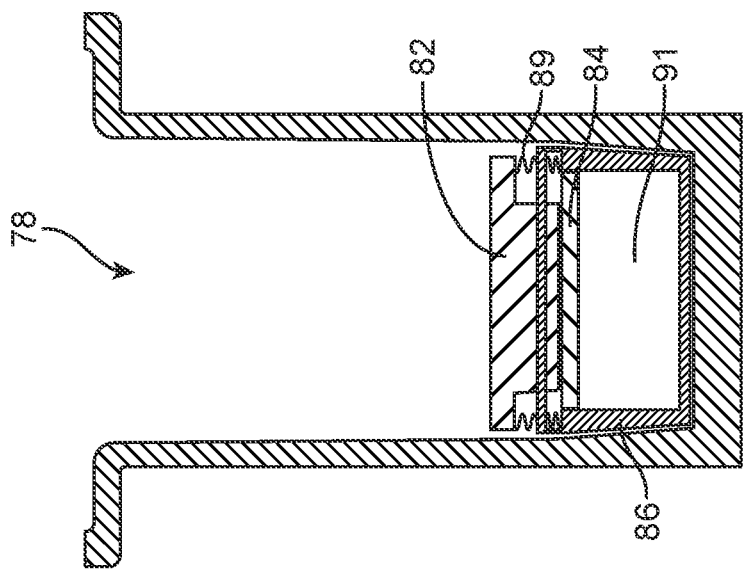
FIG. 13 depicts a cross-sectional side elevational view of the pill bottle container for FIG. 12, according to one or more embodiments herein.

Referring to FIG. 13, the top 77 opens to a cavity 78 within body 76 that extends towards the bottom 72. A sensor system 110 may be located at the bottom of the cavity and may include sensing plate 82 connected to activation plate 84. Sensing plate 82 is connected via one or more flexible compression elements 89 to circuit housing 86, which contains circuit 91. The sensor system 110 of FIG. 13 may be substantially similar to the sensing system 110 described herein with respect to FIGS. 2-8. The sensor system 110 may include an RFID system, such as a processor, power source, antenna, transmitter, reader and non-transitory memory including instruction for authenticating an RFID tag.

Figure 14:
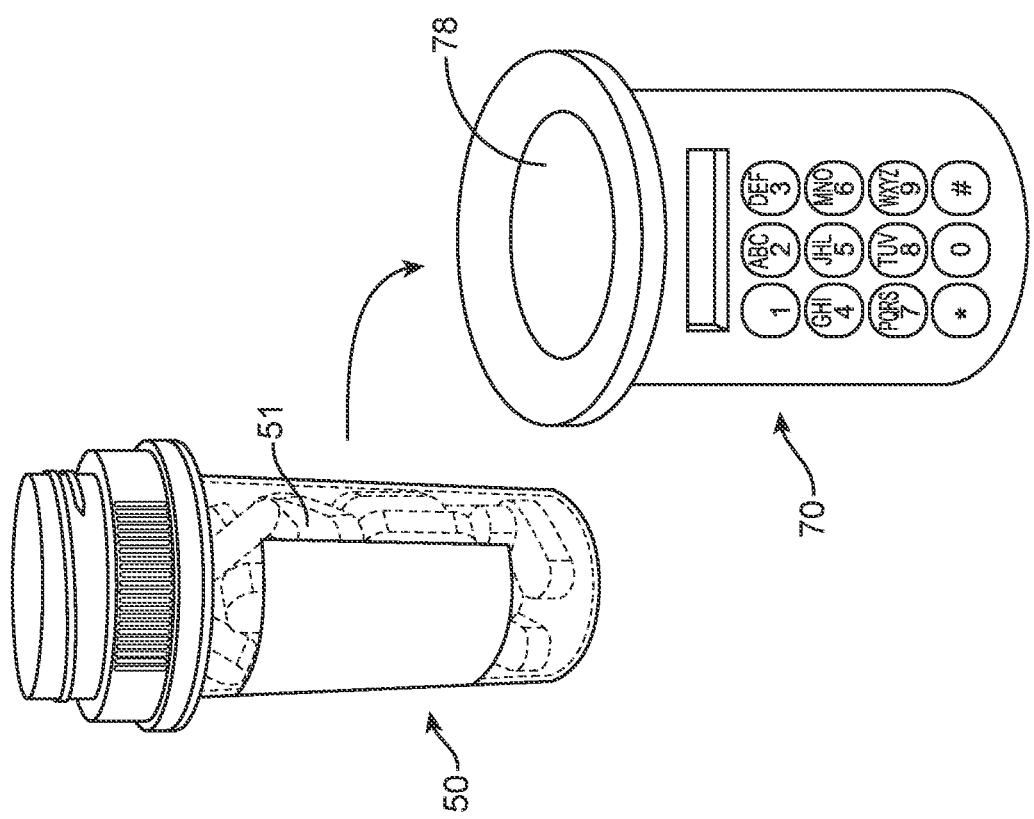
FIG. 14 depicts a pill bottle being placed in the pill bottle container, according to one or more embodiments herein.
Figure 15:
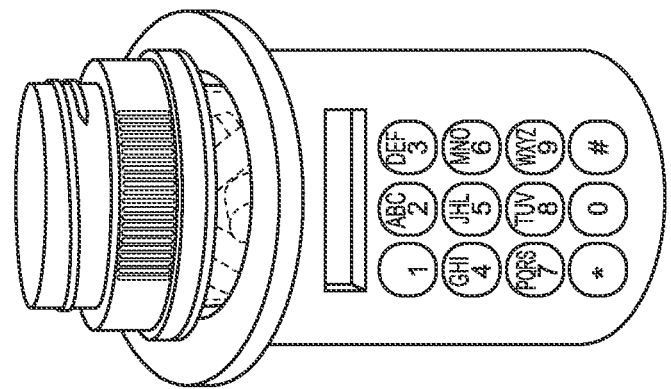
FIG. 15 depicts a perspective view of a pill bottle inside the pill bottle container, according to one or more embodiments herein.
Figure 18:
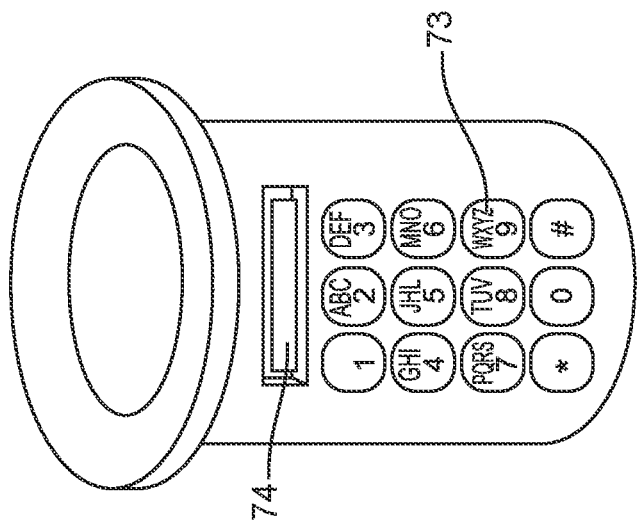
FIG. 18 depicts a perspective view of a pill bottle container after the pill bottle has been removed and the visual indicator light has been activated, according to one or more embodiments herein.
Figure 17:
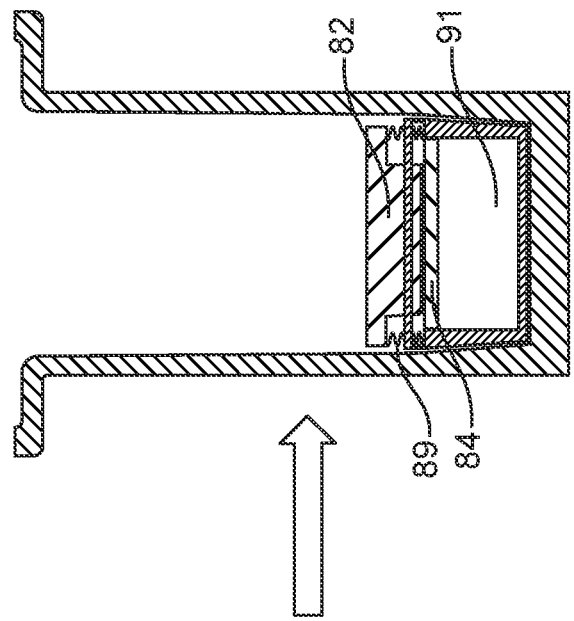
FIG. 17 depicts a cross-sectional side elevational view of the pill bottle container after the pill bottle has been removed, according to one or more embodiments herein.
Figure 16:
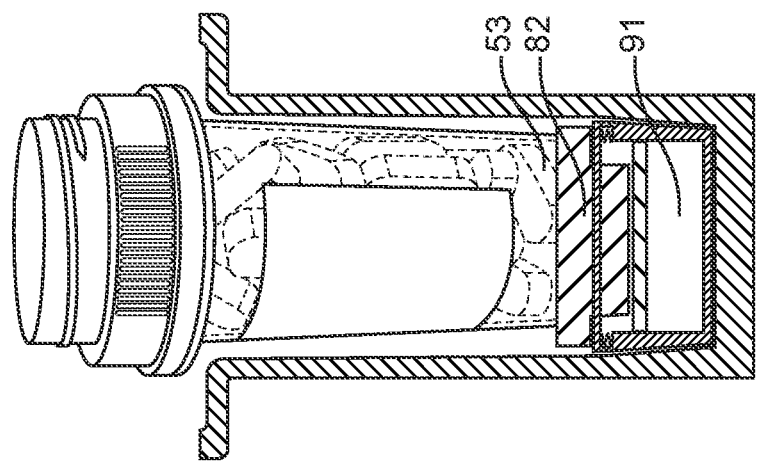
FIG. 16 depicts a cross-sectional side elevational view of a pill bottle inside the pill bottle container, according to one or more embodiments herein.

Now referring to FIGS. 14-15, upon initial use of pill bottle container, the body 51 of pharmaceutical bottle 50 is placed within the cavity 78 of the pill bottle container 70. As shown in FIG. 16, the bottom 53 of body 51 pushes sensing plate 82 and attached activation plate 84 downwards, thereby keeping circuit 91 in inactive state and the indicator 74 off. As shown in FIG. 17-18, when bottle 50 is removed from the container 70, the one or more flexible compression elements 89 urge sensing plate 82 and attached activation plate 84 upwards, thereby activating circuit 91, turning on indicator 74. To turn off indicator 74, the security code may be entered into passcode pad 73. Otherwise, the indicator 74 may remain on, even if bottle 50 is placed back into the container, indicating unauthorized access to bottle 50. The operation of the pill bottle container 70 and circuit 91 may be similar to that of the bottle 50 and cap and sensing circuit 21 and other elements of FIGS. 1-8.

Figure 19:
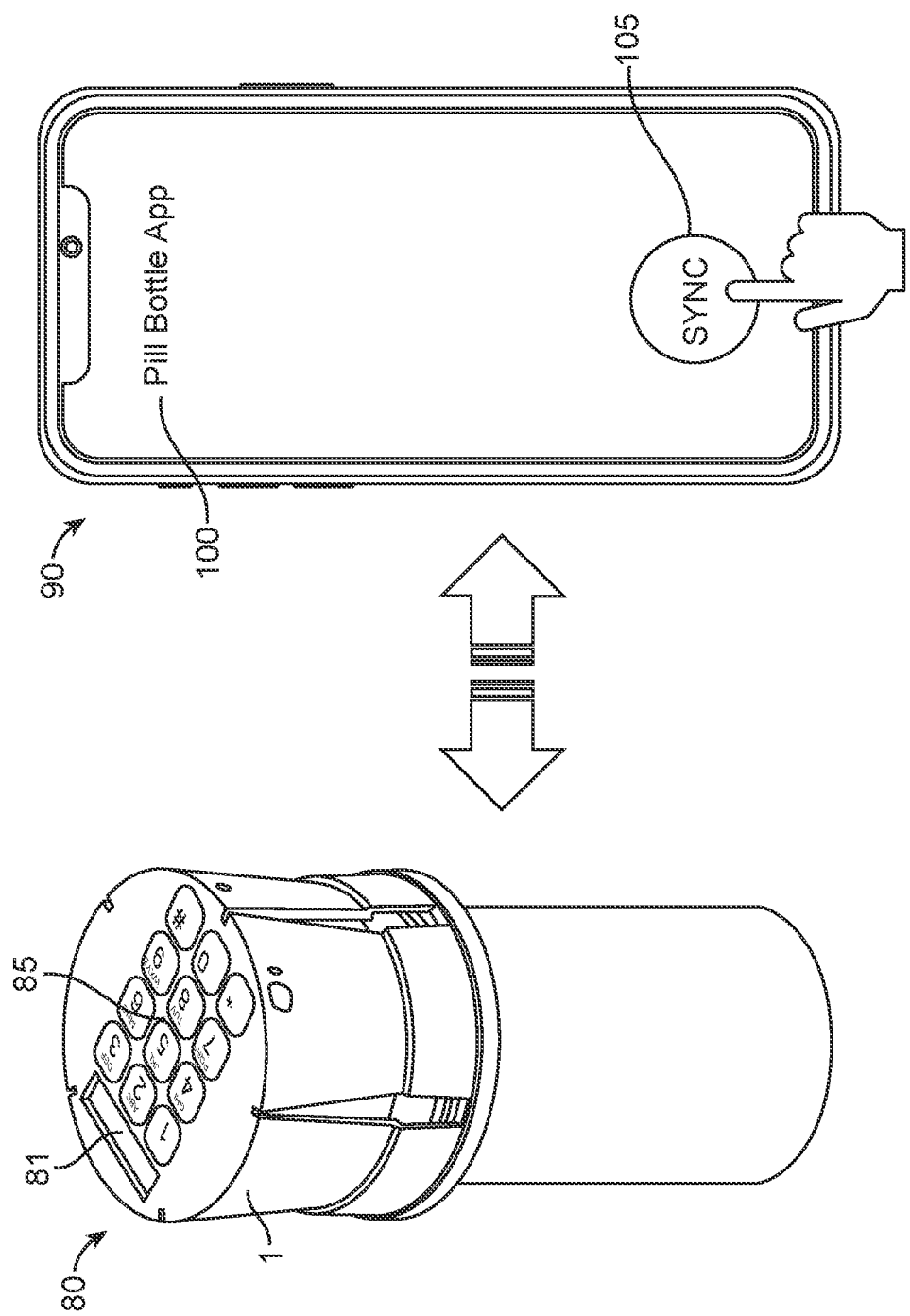
FIG. 19 depicts a perspective view of a pill bottle cap with integrated container and a partially schematic view of a smartphone with an app designed to couple the phone to the pill bottle cap and container, according to one or more embodiments herein.
Figure 20:
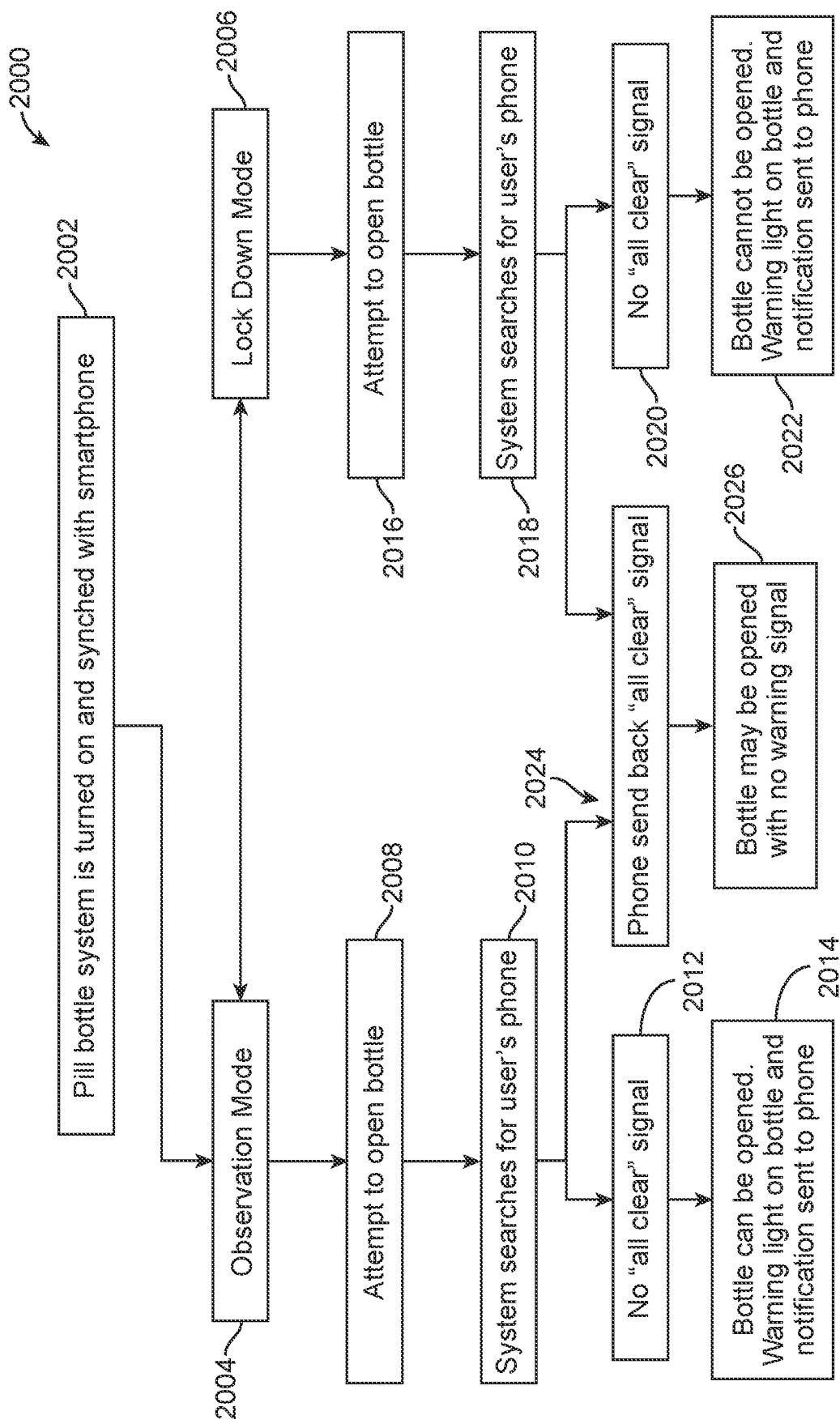
FIG. 20 depicts a method of sensing the opening of pharmaceutical bottles, according to one or more embodiments herein.

The Pill Bottle Cap/Container with Wireless Communication to Smartphone (FIGS. 19-20)

Now referring to FIG. 19, a pill bottle cap with integrated container 80, or any of the other embodiments of FIGS. 1-18 discussed herein, may have the ability to communicate with a smartphone 90 in a similar manner. After pill bottle app 100 has been installed on smartphone 90, the user may press the sync icon 105, which pairs the system 80 with the smartphone 90 so that the pill bottle cap only responds to communications with the paired smartphone. The sensor system 110 within the station may include an RFID system, such as a processor, power source, antenna, transmitter, reader and non-transitory memory including instruction for authenticating an RFID tag.

Now referring to FIG. 20 a method 2000 of operating and using a pill bottle cap or container as discussed herein is shown. At block 2002, a pill bottle system, such as a cap or container is synched with a smartphone, such as shown and described with respect to FIGS. 3 and 4. After synching as described in herein, such as, for example with respect to FIGS. 3 and 4, at block 2004, the phone may be in the default or first mode, such as an "Observation Mode", although it is contemplated that the default could alternatively, at block 2006, be in or enter a second mode, such as a "Lock Down Mode", and as indicated by the flowchart, the user may switch modes via the smartphone app. If in observation mode, at block 2008, the cap of system 80 is being or attempted to be opened. At block 2010, upon sensing an attempt to open or an opening, the system 80 may wirelessly send a signal to see if the smartphone 90 is in a prespecified vicinity. If so, the smartphone 90 at block 2024 may send an "all clear" signal to the system 80, and at block 2026 the cap can be removed without activating the visual indicator and without sending a notification to the smartphone. If the smartphone is not in the specified vicinity, at block 2012, a smartphone may not send an "all clear" signal to the system 80 and no "all clear" signal is received, and, at block 2014 system 80 may turn on its visual indicator 81 and send a notification to smartphone 90. The visual indicator may be turned off by entry of a code into keypad 81, or via the app 100.

The "Observation Mode" may be activated via the app for more specific indicators for notification; for example, the user may indicate that visual indicator activation and notification should occur if bottle is opened outside certain times and/or if bottle is opened more than a certain number of times.

In another aspect, in "Lockdown Mode", at block 2016 upon sensing an attempt to open or an opening, at block 2018, the system 80 may wirelessly send a signal to see if the smartphone 90 is in a prespecified vicinity. If an "all clear" signal is not sent from the smartphone to system at block 2020, then at block 2022, the pill bottle cap may be locked and the system and pill bottle cannot be opened, the bottle removed, or the cap removed. Also, the visual indicator may be turned on and a notification of opening an attempted opening or removal may be sent to the smartphone. Unlocking the pill bottle cap may occur via entry of a code into keypad 81, or via the app 100 installed on smartphone 90.

In another aspect, the bottle cap, bottle container, or pill bottle station communicates with either a passive or active radio frequency identification (RFID) tag worn by the user. If a passive RFID tag is used, then the bottle cap, bottle container, or pill bottle station transmits energy to the tag, which will read the signal and transmit information back, sending an "all clear" signal, either to turn off any alert or to allow the bottle to be opened. Alternatively, the RFID tag may be active, like a beacon, which transmits regular signals that can be picked up by the reader embedded in the pill bottle system when the system is in close proximity to the tag.

Figure 21:
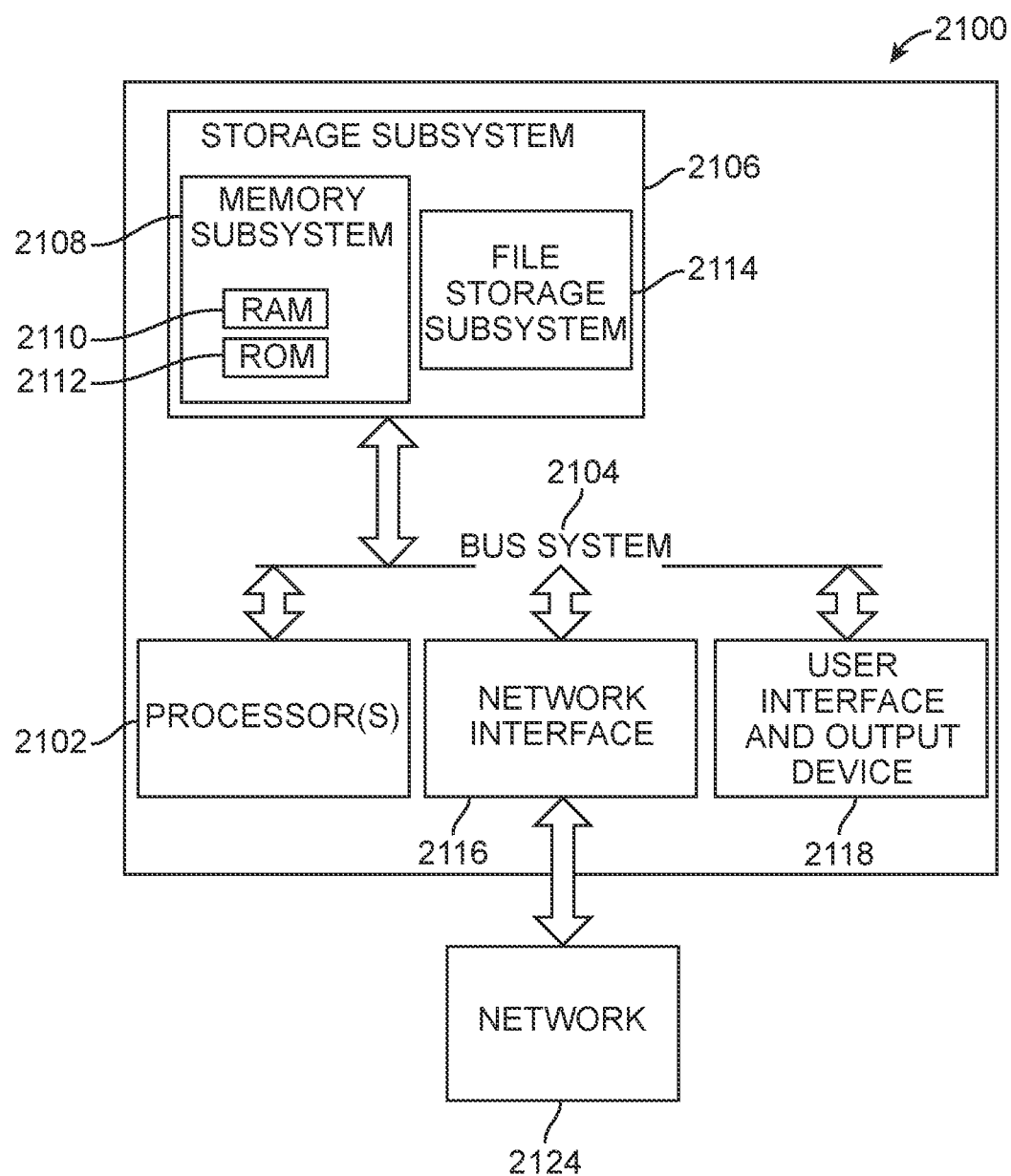
FIG. 21 depicts a simplified block diagram of a data processing system that may be used in executing methods and processes described herein, according to one or more embodiments herein.

FIG. 21 is a simplified block diagram of a data processing system 2100 that may be used in executing methods and processes described herein. The data processing system 2100 typically includes one or more processors 2102 that communicates with one or more peripheral devices via bus subsystem 2104. These peripheral devices typically include a storage subsystem 2106 (memory subsystem 2108 and file storage subsystem 2114), a set of user interface input and output devices 2118, and an interface to outside networks 2116. This interface is shown schematically as "Network Interface" block 2116, and is coupled to corresponding interface devices in other data processing systems via communication network interface 2124. Data processing system 2100 can include, for example, one or more computers, such as a personal computer, workstation, mainframe, laptop, and the like, the pill bottle cap or container or smartphone discussed herein.

The user interface input devices 2118 are not limited to any particular device, and can typically include, for example, a keyboard, pointing device, mouse, scanner, interactive displays, touchpad, joysticks, pin pads, fingerprint readers, etc. Similarly, various user interface output devices can be employed in a system of the invention, and can include, for example, one or more of a printer, display (e.g., visual, non-visual) system/subsystem, controller, projection device, audio output, and the like.

Storage subsystem 2106 maintains the basic required programming, including computer readable media, such as non-transitory computer readable media, having instructions or program modules (e.g., operating instructions, etc.), and data constructs that when executed by the processor or processors, case the system to carry out the methods described herein. The program modules discussed herein are typically stored in storage subsystem 2106. Storage subsystem 2106 typically includes memory subsystem 2108 and file storage subsystem 2114. Memory subsystem 2108 typically includes a number of memories (e.g., RAM 2110, ROM 2112, etc.) including computer readable memory for storage of fixed instructions, instructions and data during program execution, basic input/output system, etc. File storage subsystem 2114 provides persistent (non-volatile) storage for program and data files, and can include one or more removable or fixed drives or media, hard disk, floppy disk, CD-ROM, DVD, optical drives, and the like. One or more of the storage systems, drives, etc. may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

System 2100 may be located at a location remote with respect to other components of the system and can communicate information to pill bottle caps or containers, etc. discussed herein, for example, via a network interface 2124.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A system located within a pill bottle cap for sensing use of a pharmaceutical bottle, the system comprising:
   a circuit housing;
   a sensing plate mechanically coupled to the housing by one or more flexible expansion members;
   an activation plate mechanically coupled to the sensing plate;
   an electronic contact on the housing;
   an electrical circuit formed by the electronic contact on the housing and the activation plate, wherein the flexible expansion elements push against a perimeter of the circuit housing thereby pushing the activating plate into contact and electrical continuity with the electrical circuit when the cap is removing from the bottle;
   an indicator configured to indicate use of the pharmaceutical bottle;
   a user interface configured to receive user input to control the indicator; and
   a processor and memory with instructions that when execute by the processor cause the system to:
   determine that the pharmaceutical bottle has been used based on a change in the electrical circuit.

2. The system of claim 1, wherein:
   the change in the electrical circuit is an opening or closing of the electrical circuit.

3. The system of claim 2, wherein:
   one or more flexible expansion members urge the activation plate towards the electronic contact to normally close the electrical circuit and force applied to the sensing plate urges the activation plate away from the electronic contact to open the electrical circuit.

4. The system of claim 1, wherein:
   the user interface and the indicator are located at an external surface of the pill bottle cap.

5. The system of claim 1, further comprising:
   a pill bottle station; and
   a receptacle within the pill bottle station, and
   wherein the housing is located within the receptacle.

6. The system of claim 5, wherein:
   the user interface and the indicator are located at an external surface of the pill bottle station.

7. The system of claim 1, further comprising:
   a pill bottle container, the pill bottle container including a cavity shaped to receive the pharmaceutical bottle, and
   wherein the housing is located within the cavity.

8. The system of claim 7, wherein:
   the user interface and the indicator are located at an external surface of the pill bottle container.

9. The system of claim 1, wherein the indicator is a light source.

10. The system of claim 9, wherein the light source is an LED, OLED, or phosphorescent LED, TOLED, AMOLED, PMOLED, or QLED.

11. The system of claim 1, wherein the indicator is a display.

12. The system of claim 11, wherein the display is a LCD display, an LED display, or an OLED display.

13. The system of claim 1, wherein the instructions that when executed by the processor further cause the system to:
    receive user input through the user interface, the user input being a passcode;
    activate the indicator after sensing use of the pharmaceutical bottle; and
    deactivating the indicator after receiving the passcode.

14. The system of claim 1, wherein the instructions that when executed by the processor further cause the system to:
    use wireless communication to search for a user's smart phone;
    sense that the user's smart phone is nearby after sensing use of the pharmaceutical bottle; and
    suppressing the indicator when after sensing use of the pharmaceutical bottle and that the user's smart phone is nearby.

15. The system of claim 14, wherein sensing that the user's smart phone is nearby comprises receiving a message from the user's smart phone.

16. The system of claim 1, wherein the instructions that when executed by the processor further cause the system to:
    use wireless communication to search for a user's smart phone;
    sense that the user's smart phone is not nearby after sensing use of the pharmaceutical bottle; and
    activating the indicator when after sensing use of the pharmaceutical bottle and that the user's smart phone is not nearby.

17. The system of claim 14, wherein sensing that the user's smart phone is not nearby comprises failing to receive a message from the user's smart phone within a predetermined period of time.

* * * * *